(12) United States Patent
Fischer et al.

(10) Patent No.: US 7,144,250 B2
(45) Date of Patent: Dec. 5, 2006

(54) RECHARGEABLE DENTAL CURING LIGHT

(75) Inventors: Dan E. Fischer, Sandy, UT (US); Bruce S. McLean, Sandy, UT (US)

(73) Assignee: Ultradent Products, Inc., South Jordan, UT (US)

( * ) Notice: Subject to any disclaimer, the term of this patent is extended or adjusted under 35 U.S.C. 154(b) by 230 days.

(21) Appl. No.: 10/740,000

(22) Filed: Dec. 17, 2003

(65) Prior Publication Data
US 2005/0136372 A1 Jun. 23, 2005

(51) Int. Cl.
*A61C 3/00* (2006.01)
(52) U.S. Cl. .......................... 433/29; 433/77
(58) Field of Classification Search .............. 433/29, 433/215, 114, 77
See application file for complete search history.

(56) References Cited

U.S. PATENT DOCUMENTS

| | | | |
|---|---|---|---|
| 3,310,358 A | 3/1967 | Marcatili | |
| 3,666,180 A | 5/1972 | Coombs et al. | 240/41.15 |
| 3,704,928 A | 12/1972 | Coombs et al. | |
| 3,930,149 A | 12/1975 | French | |
| 4,184,196 A | 1/1980 | Moret | |
| 4,221,994 A | 9/1980 | Friedman et al. | |
| 4,229,658 A | 10/1980 | Gonser | |
| 4,245,890 A | 1/1981 | Hartman et al. | |
| 4,266,535 A | 5/1981 | Moret | |
| 4,281,366 A | 7/1981 | Wurster et al. | |
| 4,309,617 A | 1/1982 | Long | |
| 4,348,180 A | 9/1982 | Schuss | |
| 4,385,344 A | 5/1983 | Gonser | 362/32 |
| 4,392,827 A | 7/1983 | Martin | |
| 4,522,594 A | 6/1985 | Stark et al. | |
| 4,611,992 A | 9/1986 | Lokken | |
| 4,666,405 A | 5/1987 | Ericson | |
| 4,666,406 A | 5/1987 | Kanca, III | |
| 4,682,950 A | 7/1987 | Dragan | |
| 4,698,730 A | 10/1987 | Sakai et al. | |
| 4,725,231 A * | 2/1988 | Boinot et al. | 433/29 |
| 4,733,937 A | 3/1988 | Lia et al. | |
| 4,836,782 A | 6/1989 | Gonser | |
| 4,935,665 A | 6/1990 | Murata | |
| 4,948,215 A | 8/1990 | Friedman | |
| 4,952,146 A * | 8/1990 | Doty | 433/77 |
| 4,963,798 A | 10/1990 | McDermott | |
| 4,992,045 A | 2/1991 | Beisel | |
| 5,013,144 A | 5/1991 | Silverglate et al. | |

(Continued)

FOREIGN PATENT DOCUMENTS

WO  WO 00/11360  3/2000

OTHER PUBLICATIONS

U.S. Appl. No. 10/973,537, filed Oct. 26, 2004, Robert R. Scott.

(Continued)

*Primary Examiner*—Melba Bumgarne
(74) *Attorney, Agent, or Firm*—Workman Nydegger

(57) ABSTRACT

A light curing dental device is configured for curing light-curable compounds and includes a rechargeable power supply. The light curing device is configured to be received by and recharged by a recharging docking station that is connected with a dental hand piece holder tray. The recharging docking station may take the form of a dental hand piece holder. Some light curing devices can be recharged by electrical contact when they are placed within a recharging docking station. Some other light curing devices are watertight and do not have exposed electrical contacts. These other light curing devices can be recharged by the recharging docking station through induction.

4 Claims, 5 Drawing Sheets

U.S. PATENT DOCUMENTS

| | | | |
|---|---|---|---|
| 5,013,240 A | 5/1991 | Bailey et al. | |
| 5,017,140 A | 5/1991 | Ascher | |
| 5,043,634 A | 8/1991 | Rothwell, Jr. et al. | |
| 5,046,810 A | 9/1991 | Steiner et al. | 385/38 |
| 5,071,222 A | 12/1991 | Laakmann et al. | |
| 5,115,761 A | 5/1992 | Hood | |
| 5,123,845 A | 6/1992 | Vassiliadis et al. | |
| 5,139,495 A | 8/1992 | Daikuzono | |
| 5,160,194 A * | 11/1992 | Feldman | 362/109 |
| 5,161,879 A | 11/1992 | McDermott | |
| 5,275,564 A | 1/1994 | Vassiliadis et al. | |
| 5,285,318 A | 2/1994 | Gleckman | |
| 5,288,231 A | 2/1994 | Kuehn et al. | |
| 5,290,169 A | 3/1994 | Friedman et al. | |
| 5,312,249 A | 5/1994 | Kennedy | |
| 5,328,368 A | 7/1994 | Lansing et al. | |
| 5,348,552 A | 9/1994 | Nakajima et al. | |
| 5,371,826 A | 12/1994 | Friedman | |
| 5,382,799 A | 1/1995 | May | |
| 5,388,988 A | 2/1995 | Goisser et al. | |
| 5,397,892 A | 3/1995 | Abdelqader | |
| 5,415,543 A | 5/1995 | Rozmajzl, Jr. | |
| 5,420,768 A | 5/1995 | Kennedy | |
| D361,382 S | 8/1995 | Brunsell et al. | |
| 5,448,323 A | 9/1995 | Clark et al. | |
| 5,457,611 A | 10/1995 | Verderber | |
| 5,485,317 A | 1/1996 | Perissinotto et al. | |
| 5,521,392 A | 5/1996 | Kennedy et al. | |
| 5,527,261 A | 6/1996 | Monroe et al. | |
| 5,616,141 A | 4/1997 | Cipolla | |
| 5,634,711 A | 6/1997 | Kennedy et al. | |
| 5,636,988 A | 6/1997 | Murayama | 433/118 |
| 5,660,461 A | 8/1997 | Ignatius et al. | |
| 5,669,769 A | 9/1997 | Disel | |
| D385,051 S | 10/1997 | Wu | |
| D385,630 S | 10/1997 | Lieb et al. | |
| 5,698,866 A | 12/1997 | Doiron et al. | |
| 5,711,665 A | 1/1998 | Adam et al. | |
| 5,733,029 A | 3/1998 | Monroe | |
| 5,749,724 A | 5/1998 | Cheng | |
| 5,759,032 A | 6/1998 | Bartel | |
| 5,762,605 A | 6/1998 | Cane et al. | |
| 5,768,458 A | 6/1998 | Ro et al. | |
| 5,772,643 A | 6/1998 | Howell et al. | |
| 5,782,553 A | 7/1998 | McDermott | |
| 5,791,898 A | 8/1998 | Maissami | |
| 5,797,740 A | 8/1998 | Lundvik | |
| 5,803,729 A | 9/1998 | Tsimerman | |
| 5,880,839 A | 3/1999 | Ishizuka et al. | |
| 5,885,082 A | 3/1999 | Levy | |
| 5,897,314 A | 4/1999 | Hack et al. | 433/29 |
| 5,905,268 A | 5/1999 | Garcia et al. | |
| 5,908,294 A | 6/1999 | Schick et al. | |
| 5,908,295 A | 6/1999 | Kawata | |
| 5,912,470 A | 6/1999 | Eibofner et al. | |
| 5,921,777 A | 7/1999 | Dorman | |
| 5,971,755 A | 10/1999 | Liebermann et al. | |
| 5,975,895 A | 11/1999 | Sullivan | |
| 6,001,058 A | 12/1999 | Sano et al. | |
| 6,008,264 A | 12/1999 | Ostler et al. | |
| 6,019,482 A | 2/2000 | Everett | |
| 6,019,599 A | 2/2000 | Völcker et al. | |
| 6,028,694 A | 2/2000 | Schmidt | |
| 6,033,087 A | 3/2000 | Shozo et al. | |
| 6,033,223 A | 3/2000 | Narusawa et al. | |
| 6,036,336 A | 3/2000 | Wu | |
| 6,059,421 A | 5/2000 | White et al. | |
| 6,068,474 A | 5/2000 | Senn et al. | |
| 6,077,073 A | 6/2000 | Jacob | |
| 6,086,366 A | 7/2000 | Mueller et al. | |
| 6,089,740 A | 7/2000 | Forehand et al. | |
| 6,095,661 A | 8/2000 | Lebens et al. | |
| 6,095,812 A | 8/2000 | Senn et al. | |
| 6,099,520 A | 8/2000 | Shimoji | |
| 6,102,696 A | 8/2000 | Osterwalder et al. | |
| 6,103,203 A | 8/2000 | Fischer | |
| 6,123,545 A | 9/2000 | Eggler et al. | |
| 6,155,823 A | 12/2000 | Nagel | |
| 6,159,005 A | 12/2000 | Herold et al. | |
| 6,200,134 B1 | 3/2001 | Kovac et al. | |
| 6,208,788 B1 | 3/2001 | Nosov | |
| 6,270,343 B1 | 8/2001 | Martin | |
| 6,280,187 B1 | 8/2001 | Stone | |
| 6,282,013 B1 | 8/2001 | Ostler et al. | |
| 6,318,996 B1 | 11/2001 | Melikechi et al. | |
| 6,322,358 B1 | 11/2001 | Senn et al. | |
| 6,325,623 B1 | 12/2001 | Melnyk et al. | |
| 6,328,456 B1 | 12/2001 | Mize | |
| 6,331,111 B1 | 12/2001 | Cao | |
| 6,361,192 B1 | 3/2002 | Fussell et al. | |
| 6,361,489 B1 | 3/2002 | Tsai | |
| 6,398,398 B1 | 6/2002 | Moschkowitz | |
| 6,402,511 B1 | 6/2002 | Calderwood | |
| 6,417,917 B1 | 7/2002 | Jung et al. | |
| 6,419,483 B1 | 7/2002 | Adam et al. | |
| 6,439,888 B1 | 8/2002 | Boutoussov et al. | |
| 6,465,961 B1 | 10/2002 | Cao | |
| 6,468,077 B1 | 10/2002 | Melikechi et al. | |
| 6,478,447 B1 | 11/2002 | Yen | |
| 6,482,004 B1 | 11/2002 | Senn et al. | |
| 6,485,301 B1 | 11/2002 | Gemunder et al. | |
| 6,511,317 B1 | 1/2003 | Melikechi et al. | |
| 6,511,321 B1 | 1/2003 | Trushkowsky et al. | |
| 6,514,075 B1 | 2/2003 | Jacob | |
| 6,522,086 B1 | 2/2003 | Gemunder et al. | 315/291 |
| 6,611,110 B1 | 8/2003 | Fregoso | |
| 6,635,363 B1 | 10/2003 | Duclos et al. | 428/690 |
| 6,666,875 B1 * | 12/2003 | Sakurai et al. | 606/169 |
| 6,692,251 B1 | 2/2004 | Logan et al. | |
| 6,692,252 B1 | 2/2004 | Scott | |
| 6,702,576 B1 | 3/2004 | Fischer et al. | 433/29 |
| 6,709,128 B1 | 3/2004 | Gordon et al. | |
| 6,719,558 B1 | 4/2004 | Cao | |
| 6,719,559 B1 | 4/2004 | Cao | |
| 6,755,647 B1 | 6/2004 | Melikechi et al. | 433/29 |
| 6,755,648 B1 | 6/2004 | Cao | |
| 6,755,649 B1 | 6/2004 | Cao | |
| 6,783,362 B1 | 8/2004 | Cao | 433/29 |
| 6,890,175 B1 | 5/2005 | Fischer et al. | 433/29 |
| 6,940,659 B1 | 9/2005 | McLean et al. | 359/709 |
| 2001/0038992 A1 | 11/2001 | Otsuka | |
| 2001/0046652 A1 | 11/2001 | Ostler et al. | |
| 2001/0055451 A1 | 12/2001 | Kuhara et al. | |
| 2002/0073921 A1 | 6/2002 | Russell et al. | |
| 2002/0085372 A1 | 7/2002 | Lehrer | |
| 2002/0093833 A1 | 7/2002 | West | |
| 2002/0102513 A1 | 8/2002 | Plank | |
| 2002/0115037 A1 | 8/2002 | Cao | |
| 2002/0133970 A1 | 9/2002 | Gordon et al. | |
| 2002/0147383 A1 | 10/2002 | Weber et al. | |
| 2002/0163317 A1 | 11/2002 | Cao | |
| 2002/0167283 A1 | 11/2002 | Cao | |
| 2002/0168306 A1 | 11/2002 | Cao | |
| 2002/0168604 A1 | 11/2002 | Cao | |
| 2002/0168605 A1 | 11/2002 | Cao | |
| 2002/0168606 A1 | 11/2002 | Cao | |
| 2002/0168607 A1 | 11/2002 | Cao | |
| 2002/0168608 A1 | 11/2002 | Cao | |
| 2002/0172912 A1 | 11/2002 | Cao | |
| 2002/0172913 A1 | 11/2002 | Cao | |
| 2002/0172914 A1 | 11/2002 | Cao | |
| 2002/0172915 A1 | 11/2002 | Cao | |
| 2002/0172916 A1 | 11/2002 | Cao | |
| 2002/0172917 A1 | 11/2002 | Cao | |

| | | |
|---|---|---|
| 2002/0175352 A1 | 11/2002 | Cao |
| 2002/0175628 A1 | 11/2002 | Cao |
| 2002/0177095 A1 | 11/2002 | Cao |
| 2002/0177096 A1 | 11/2002 | Cao |
| 2002/0177099 A1 | 11/2002 | Cao |
| 2002/0180368 A1 | 12/2002 | Cao |
| 2002/0181947 A1 | 12/2002 | Cao |
| 2002/0182561 A1 | 12/2002 | Cao |
| 2002/0182562 A1 | 12/2002 | Cao |
| 2002/0187454 A1 | 12/2002 | Melikechi et al. |
| 2002/0187455 A1 | 12/2002 | Melikechi et al. |
| 2002/0190659 A1 | 12/2002 | Cao |
| 2002/0190660 A1 | 12/2002 | Cao |
| 2002/0197582 A1 | 12/2002 | Cao |
| 2003/0001507 A1 | 1/2003 | Cao |
| 2003/0036031 A1 | 2/2003 | Lieb et al. |
| 2003/0038291 A1 | 2/2003 | Cao |
| 2003/0039119 A1 | 2/2003 | Cao |
| 2003/0039120 A1 | 2/2003 | Cao |
| 2003/0039122 A1 | 2/2003 | Cao |
| 2003/0040200 A1 | 2/2003 | Cao |
| 2003/0081430 A1 | 5/2003 | Becker |
| 2003/0133203 A1 | 7/2003 | McLean et al. |
| 2003/0133298 A1 | 7/2003 | Cao |
| 2003/0142413 A1 | 7/2003 | McLean et al. |
| 2003/0147254 A1 | 8/2003 | Yoneda et al. |
| 2003/0147258 A1 | 8/2003 | Fischer et al. |
| 2003/0148242 A1 | 8/2003 | Fischer et al. |
| 2003/0152885 A1 | 8/2003 | Dinh |
| 2003/0186195 A1 | 10/2003 | Comfort et al. |
| 2003/0215766 A1 | 11/2003 | Fischer et al. |
| 2003/0218880 A1 | 11/2003 | Brukilacchio |
| 2003/0219693 A1 | 11/2003 | Cao |
| 2003/0219694 A1 | 11/2003 | Bianchelti et al. |
| 2003/0235800 A1 | 12/2003 | Qadar |
| 2004/0033033 A1 | 2/2004 | Hoshino et al. |
| 2004/0059197 A1* | 3/2004 | Yamashita et al. ......... 600/300 |
| 2004/0076921 A1 | 4/2004 | Gofman et al. ............. 433/29 |
| 2004/0101802 A1 | 5/2004 | Scott ........................ 433/29 |
| 2004/0121280 A1 | 6/2004 | Fischer et al. ............. 433/29 |
| 2004/0152038 A1 | 8/2004 | Kumagai et al. ........... 433/29 |
| 2004/0201980 A1 | 10/2004 | Fischer et al. ............. 362/84 |
| 2004/0203312 A1 | 10/2004 | Bortscheller et al. ....... 445/24 |
| 2005/0042570 A1 | 2/2005 | Fischer et al. ............. 433/29 |
| 2005/0142514 A1 | 6/2005 | Scott ........................ 433/29 |

OTHER PUBLICATIONS

U.S. Appl. No. 11/184,433, filed Jul. 19, 2005, Robert S. Scott.
U.S. Appl. No. 11/200,988, filed Aug. 10, 2005, Robert R. Scott.
U.S. Appl. No. 11/294,159, filed Dec. 5, 2005, Robert R. Scott.
U.S. Appl. No. 60/304,324, filed Jul. 10, 2001, Densen Cao.
"LUXoMAX the Latest News from Akeda Dental", Akeda Dental A/S, www.akeda.dk (Oct. 1, 2001).
"New Sandia UV LEDs emit short-wavelength, high power output", Sandia Laboratories, http://www.eurekalert.org/pub_releases/2003-11/dnl-nsu111803.php (Nov. 18, 2003).

* cited by examiner

RECHARGEABLE DENTAL CURING LIGHT

BACKGROUND OF THE INVENTION

1. The Field of the Invention

The present invention is related to light curing devices and, more particularly, to rechargeable light curing devices.

2. The Relevant Technology

In the field of dentistry, dental cavities are often filled and/or sealed with photosensitive compounds that are cured when they are exposed to radiant energy, such as visible light. These compounds, commonly referred to as light-curable compounds, are placed within dental cavity preparations or onto dental surfaces where they are subsequently irradiated by light curing dental devices.

Some light curing devices are powered by batteries; others are powered through cords coupled to standard electrical outlets. Although corded light curing devices can be useful, their portability can be somewhat limited by the length of the cord to which they are attached. Accordingly, some dental practitioners have found battery powered light curing devices to be desirable because they are not immediately constrained by cords. However, existing battery powered light curing devices are not configured to securely mount to standard dental hand piece holding trays. Instead, existing battery powered light curing devices are typically set down in an insecure manner on the dental tray where the dental practitioner is working. This, however, can be somewhat undesirable because the curing-device can be contaminated from other objects or compounds that may also be setting on the dental tray. It also increases the chances that the curing-device can be accidentally knocked to the floor, where damage or further contamination can occur.

Mounting the curing-device away from the dental tray can also be somewhat undesirable because the dental practitioner who is seated at the dental tray, away from the curing-device mounting station, may not be able to easily and conveniently reach the light curing device when desired.

Yet another problem experienced with existing battery-powered and rechargeable light curing devices is that they are not water tight, thereby increasing the difficulty of thoroughly cleaning the light curing devices without potentially causing water damage to sensitive internal components.

Accordingly, in view of the foregoing, there is currently a need in the art for improved dental light curing devices and, more particularly, to rechargeable dental light curing devices.

BRIEF SUMMARY OF THE INVENTION

The present invention is directed to a rechargeable dental light curing device that is configured to mount to a standard dental hand piece holding tray.

In one embodiment, the light curing device includes a body that is configured to be held in the hand of a dental practitioner and that extends between a mountable end portion and a light-emitting end portion. The mountable end portion is configured in size and shape to fit in a standard holder of a dental hand piece holding tray and the light-emitting end portion is configured to emit the light that is generated by a light source, such as, but not limited to, an LED light source.

The power supply of the light curing device can be recharged when the mountable end portion of the light curing device is placed within the receiving end of a recharging docking station, such that the electrical contacts of the light curing devices electrically couple with the corresponding electrical contacts of the recharging docking station.

In other embodiment, the light curing device comprises a body that is water-tight, with no exposed electrical contacts for recharging. Rather, the light curing device is configured to be recharged by induction through the mountable end portion or another portion of the light curing device.

These and other advantages and features of the present invention will become more fully apparent from the following description and appended claims, or may be learned by the practice of the invention as set forth hereinafter.

BRIEF DESCRIPTION OF THE DRAWINGS

To further clarify the above and other advantages and features of the present invention, a more particular description of the invention will be rendered by reference to specific embodiments thereof which are illustrated in the appended drawings. It is appreciated that these drawings depict only typical embodiments of the invention and are therefore not to be considered limiting of its scope. The invention will be described and explained with additional specificity and detail through the use of the accompanying drawings in which.

DETAILED DESCRIPTION OF THE PREFERRED EMBODIMENTS

The term "dental hand piece," as used herein, generally refers to a handheld dental device that engages rotary instruments for cutting, cleaning, polishing or otherwise treating teeth. The term "dental hand piece" is a term of art well known in the dental industry. Nonlimiting examples of dental hand pieces include high speed turbines, low speed turbines, ultrasonic devices, and 3-way syringes. Dental hand pieces are typically driven by pneumatic, electric, and ultrasonic mechanisms.

The term "dental hand piece holding tray" generally refers to a tray configured with slots or holding devices specifically configured in shape and size for holding conventional dental hand pieces. Dental hand piece holding trays, which are well-known to those skilled in the art, are placed proximate or mounted directly to dental chairs for facilitating access to dental hand pieces held by the holding trays.

The terms "holding slot" and "holder," which are used interchangeably herein, generally refer to devices configured in size and shape to securely hold a dental hand piece. A holding slot is a typical feature of a dental hand piece holding tray.

The term "induction," refers to electromagnetic recharging, or any other similar recharging method that can be utilized to recharge a power supply without the use of exposed electrical contacts and that will enable the light curing device to comprise a water-tight body.

Figure 1:
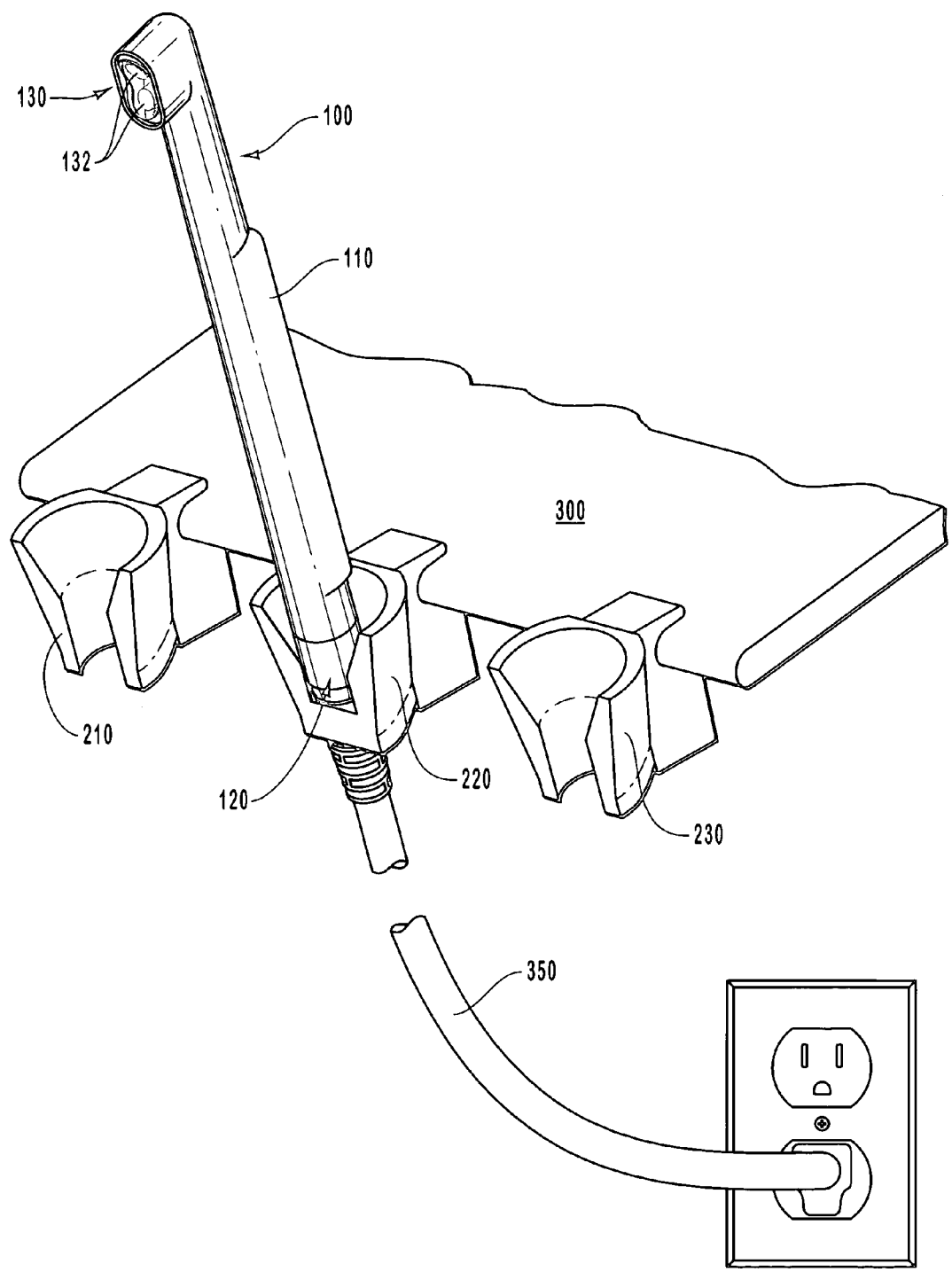
FIG. 1 is a perspective view illustrating a dental hand piece holding tray having three hand piece holders and a dental light curing device mounted within a hand piece holders comprising an electrical recharging station.

Reference is first made to FIG. 1, which illustrates one embodiment of the dental light curing device of the invention. As shown, the dental device 100 has the general configuration of a dental hand piece with a sleek and slender body 110 that extends from a mountable end portion 120 to a light-emitting end portion 130.

The light-emitting end portion 130 is configured to emit radiant energy suitable for curing a light-curable compound. Accordingly, the light-emitting end portion 130 can include any number of lenses, shields, filters, and light guides that are necessary to emit or otherwise disperse radiant energy that is produced by a suitable light source. The light source used to emit or generate the radiant energy can include an LED light source, such as the dual LEDs 132 that are presently illustrated, or any other light generating source, including, but not limited to LED arrays and bulbs. It will be appreciated that although the dual LEDs 132 are presently illustrated to be disposed at the light-emitting end portion of the light curing device, the light source of the light curing device may be disposed at any point in or on the light curing device 100.

During periods of non-use, it may be desirable to mount the light curing device 100 in a secure location proximate the dental practitioner, such as at a dental tray 300 that is being utilized by the dental practitioner. To facilitate the manner in which the light curing device 100 is mounted, the mountable end portion 120 of the light curing device is configured in size and shape to fit in a standard holder of a dental hand piece holding tray, such as, for example, hand piece holders 210, 220, or 230 of dental tray 300. One benefit of providing the light curing device 100 with a mountable end portion 120, as described above, is that the light curing device 100 can readily be moved between and secured in different tray holders, depending on the needs of the dental practitioner. In addition to being convenient, the act of securing the light curing device 100 at the dental tray 300 can also be practical, inasmuch as it can reduce the likelihood the light curing device will be accidentally dropped to the floor.

In one embodiment, the light curing device 100 is also configured with a rechargeable power supply, not shown, that is housed within the body of the light curing device. The internal power supply of the light curing device 100 can be recharged through electrical contact with a recharging station.

According to one embodiment, the recharging station is integrated with or secured to a dental hand piece holder tray 300. This enables the light curing device 100 to be simultaneously mounted and recharged at the tray 300. In one embodiment, the recharging station is integrated or connected directly to a holder of the tray, such that the light curing device 100 can be recharged while securely being held within the holder/recharger. For example, the holder 220 can be configured with electrical charging components that enable a power supply connected to the holder 220 to recharge the light curing device 100. Electrical current can be supplied to the recharging docking station (e.g., holder 220) through a power cord 350, as shown, or through any other adequate power transfer means.

Figure 2:
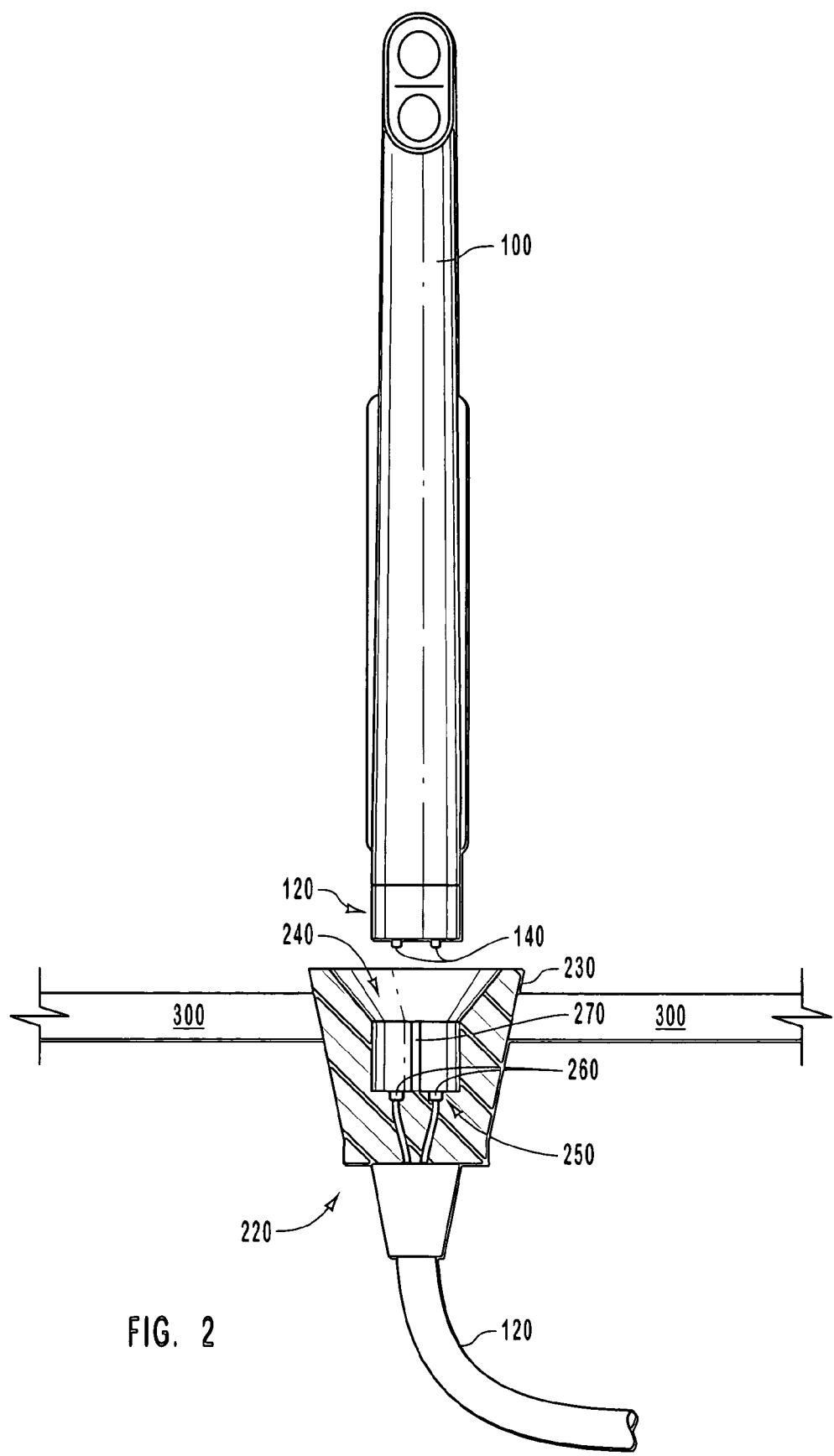
FIG. 2 is a front view of the light curing device of FIG. 1 and a partial cutaway view of one embodiment of a hand piece holder positioned below the light curing device and that is configured to receive and recharge the light curing device.

FIG. 2 illustrates how the recharging docking station/holder 220 is configured with a mounting body structure 230 that is configured to frictionally engage the mountable end portion 120 of the light curing device 100. In particular, mounting body structure 230 is formed with an internal cavity 240 that is sized and shaped conformingly to the mountable end portion 120 of the light curing device 100, such that when the mountable end portion 120 is inserted within the cavity 240 of the holder 220, the mounting body structure 230 securely holds the light curing device 100 in a desired placement therein.

FIG. 2 also illustrates how the recharging docking station 220 also includes recharging means 250 for electrically recharging the power supply of the light curing device when the mountable end portion 120 of the light curing device 100 is received within the mounting body structure 230 of the recharging docking station 220. The recharging means are presently illustrated to include electrical contacts 260 that are configured to electrically couple with electrical pins 140 that extend away from the light curing device 100.

To facilitate alignment of the light curing device within the recharging docking station 220, the recharging docking station 220 can be configured with an alignment structure, such as the illustrated groove 270 that is formed within the mounting body structure 230 of the recharging docking station 220. It will be appreciated that this groove 270 can be configured to receive a pin or other protrusion (not shown) that extends from the light curing device 100 during proper placement of the mountable end portion 120 of the light curing device within the recharging docking station 220.

Figure 3:
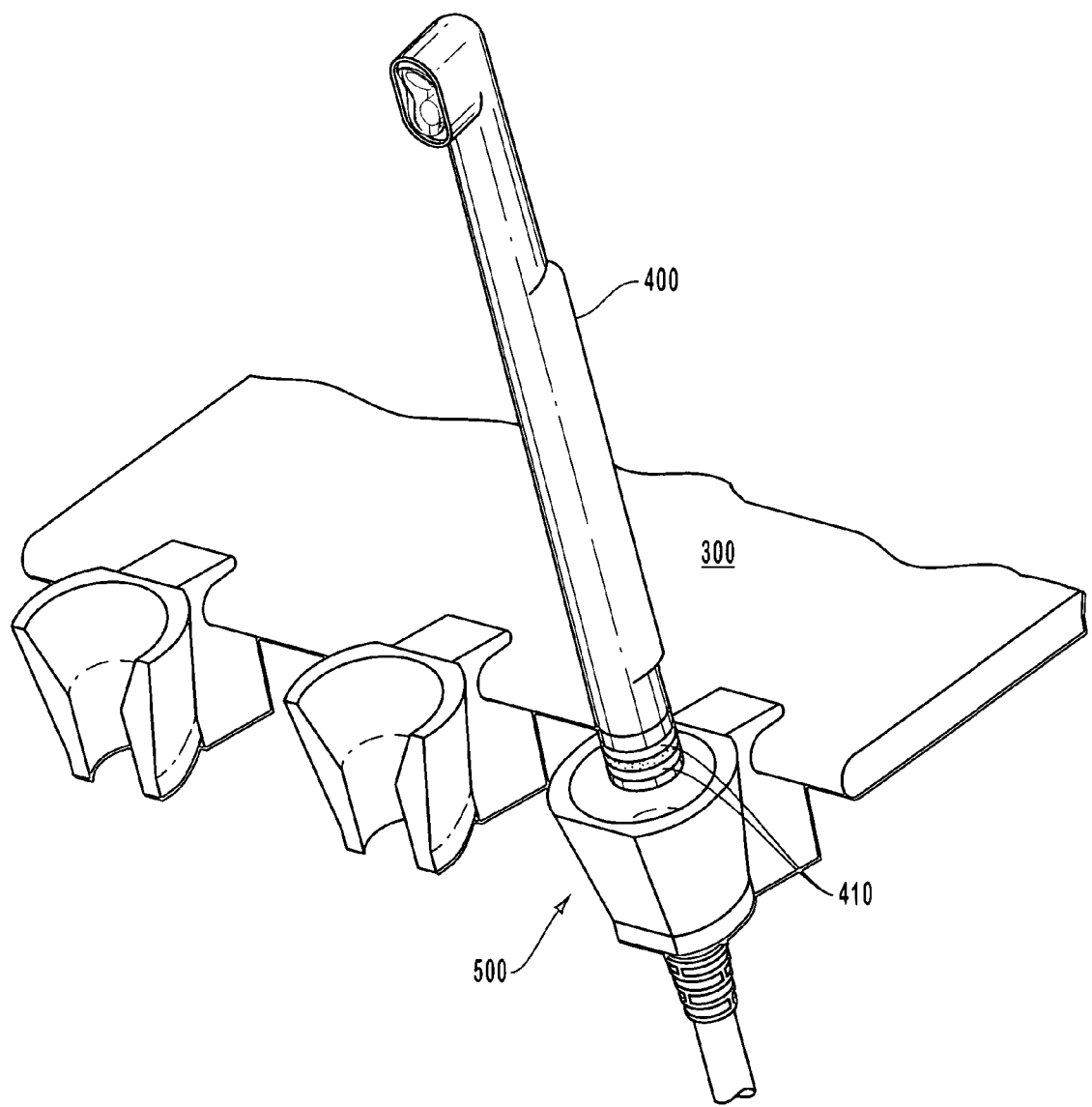
FIG. 3 is a perspective view illustrating a dental hand piece holding tray having three hand piece holders and a dental light curing device configured to be received and recharged within one of the hand piece holders that is configured to recharge the light curing device.

In another embodiment, shown in FIG. 3, rotational alignment of the light curing device 400 during placement within the recharging docking station 500 is less important and can therefore be neglected, thereby increasing the ease of placing the light curing device within the recharging docking station. This can be accomplished, for example, by utilizing recharging means that are configured to couple with electrical contacts 410 that circumferentially extend around the light curing device 400, as shown in FIG. 4.

Figure 4:
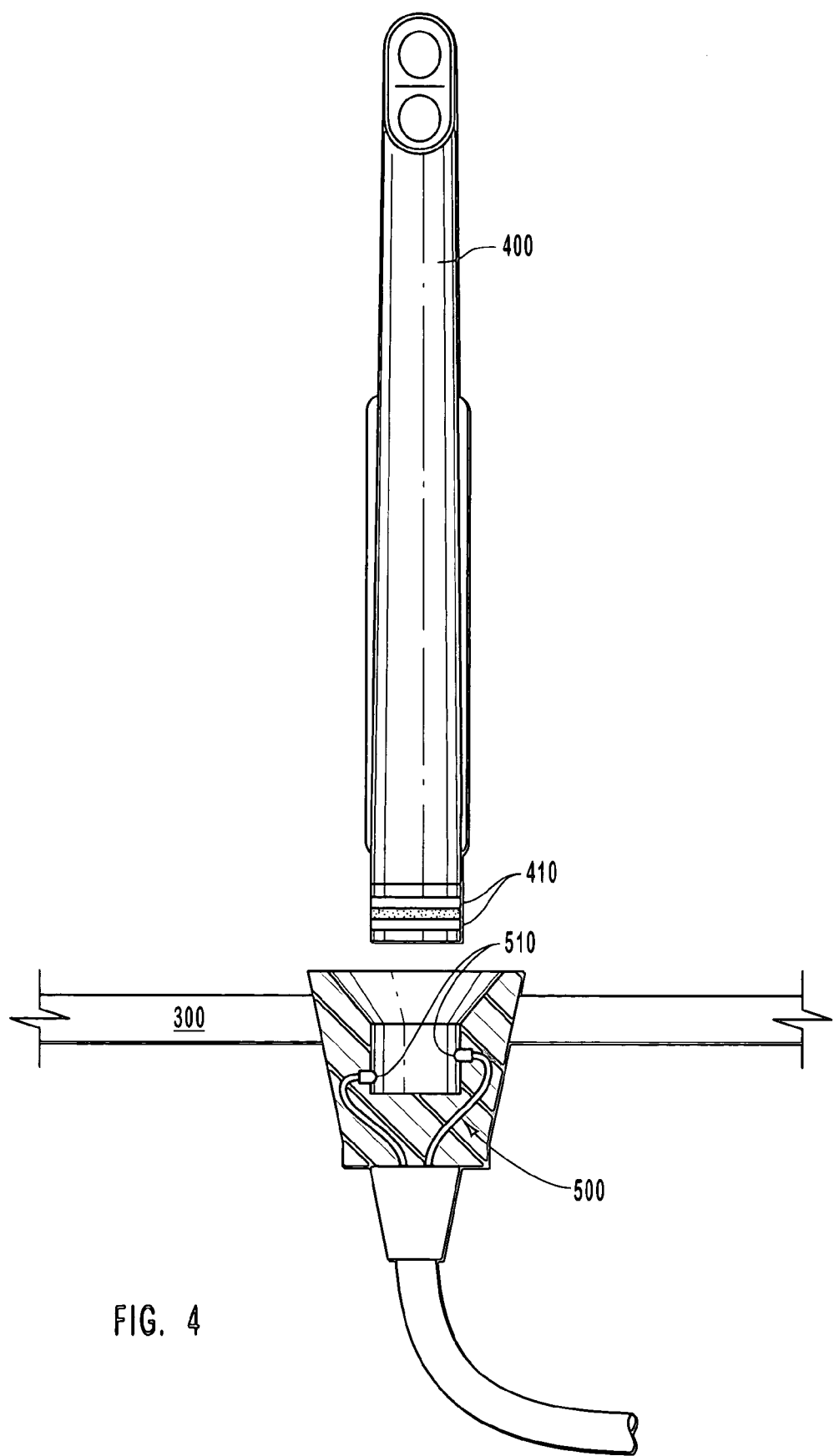
FIG. 4 is a front view of the light curing device of FIG. 3 and a partial cutaway view of one embodiment of a hand piece holder positioned below the light curing device and that is configured to receive and recharge the light curing device.

In particular, as shown in FIG. 4, the recharging docking station 500 can be configured with recharging means 500 comprising electrical contacts 510 that are positioned at relatively different heights. This will enable the electrical contacts 510 to engage the different electrical contacts 410 that are correspondingly positioned on the light curing device at different heights once the light curing device 400 is mounted within the recharging docking station 500.

In yet another embodiment, not shown, the light curing device can be configured with a body that is water-tight, without any exposed electrical contacts. In such an embodiment, the rechargeable power supply of the light curing device can be configured with components that enable recharging of the power supply through induction. To enable recharging through induction, the light curing device can include electromagnetic components (not shown) that interact with electromagnetic components (not shown) of the recharging docking station.

In one embodiment, the electromagnetic components of the light curing device react to magnetic fields that are created by the flow of current through at least some of the electromagnetic components of the recharging docking station. To generate the desired magnetic fields, current can pulsate through the electromagnetic components of the recharging docking station or the electromagnetic components of the recharging docking station can be moved relative to the electromagnetic components of the light curing device, all the while current is steadily flowing through the electromagnetic components of the recharging docking station. As will be appreciated by those of skill in the art, this can create a flow of current in the electromagnetic components of the light curing device that can be used to charge the rechargeable power supply and to power the light curing device.

One benefit of recharging the light curing device through induction is that it facilitates manufacturing the light curing device with a water-tight housing, since no electrical contacts need to be exposed outside of the body. It will also be appreciated that a water-tight body can be useful for enabling the light curing device to be cleaned without risking damage to the electrical contacts, and while reducing any chance internal components will be exposed and damaged by exposure to water and other solutions during cleaning. To provide water-tight capabilities, the body of the light curing device can be composed of a plastic, such as a polyurethane, polyester, polycarbonate, nylon, Teflon, other plastics, and combinations thereof.

As described above, the light curing devices of the invention are configured to be recharged by a recharging docking station that can be mounted to a dental hand piece holding tray, such as to a dental hand piece holder of a dental tray. Rotational alignment of the light curing device within the recharging docking station can be mandated or neglected, according to the various embodiments that are described herein. In some embodiments, the light curing device can also be recharged through induction, thereby eliminating the need to maintain exposed electrical contacts.

Although the embodiments that are shown and described herein do not describe or show power adapters or other specific electrical components, it will be appreciated that these components can be incorporated within the light curing device and/or recharging docking station as desired. A power adapter, for example, can be incorporated into the recharging docking station, remotely located from the recharging docking station (e.g., down line on the power cord 350), or within the light curing device. It will also be appreciated, that although the power cord 350 has been shown to be integrally connected to the recharging docking station, that the power cord may be detachably connectable to the recharging docking station. The power cord may also be integrally disposed within the dental tray and dental station, thereby eliminating any risk the cord will be tripped over or otherwise obstruct movement of the dental practitioner.

In yet other embodiments, the recharging docking station can be configured to set on a relatively flat surface, such as a counter top or dental tray. Such an embodiment, shown in FIGS. 5 and 6, can be particularly useful when the dentist does not wish to affix the recharging docking station to the dental tray, as described above, for various reasons.

Figures 5, 6:
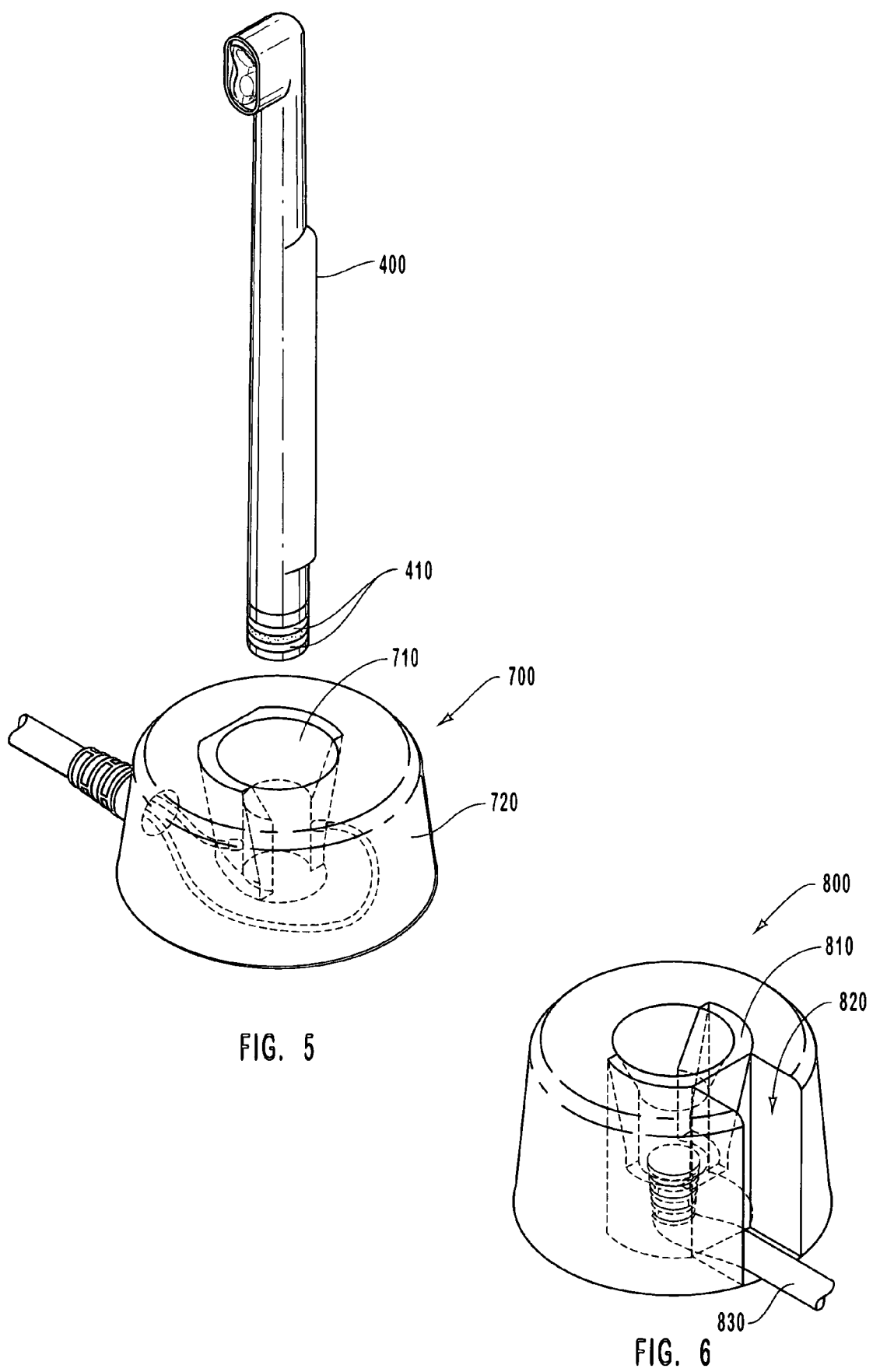
FIG. 5 illustrates a perspective view of the light curing device of FIG. 3 and a perspective view of a recharging unit encapsulating a hand piece holder that is configured to receive and recharge the light curing device.
FIG. 6 illustrates a perspective view of a recharging unit including a hand piece holder configured to recharge a light curing device and a housing that is detachably connected to the hand piece holder.

FIG. 5 illustrates one embodiment of a light curing device 400 having electrical contacts 410, as shown and described in FIGS. 3 and 4. The illustrated recharging docking station 700 also includes a hand piece holder 710 that is configured to electrically and physically couple with the end of the light curing device 400, as described in regard to FIGS. 3 and 4. However, unlike the earlier embodiments, the presently illustrated recharging docking station 700 includes a housing 720 that is connected with the hand piece holder 710 in such a way that the recharging docking station 700 is configured to set on a relatively flat surface in an upright position. The size, shape and weight of the housing is also configured to support the recharging docking station 700 in an upright position even when the light curing device 400 is mounted within the hand piece holder 710.

The recharging docking station 700 can be assembled during manufacture in such a way that the dental practitioner need not even know about or have to worry about the connection between the hand piece holder 710 and the housing 720. In fact, the housing 720 can be configured to completely encapsulate the hand piece holder 710, as shown. One benefit of this embodiment is that a practitioner can select from different form factors of the recharging docking station while still enabling the manufacturer to utilize the utility and functionality provided by a hand piece holder 710 that is already configured to electrically and physically couple with the light curing device. Accordingly, the manufacturer simply needs to manufacture the housing 720 and assemble 720 the housing to the hand piece holder 710. In some instances, slight modification to the hand piece holder 710 may also be required though.

In another embodiment, shown in FIG. 6, the recharging docking station 800 can be configured with a hand piece holder 810 that is detachably connectible to the housing 810 such that the practitioner can manually place the hand piece holder 810 within the housing. To accommodate such an embodiment, the housing 810 is configured with a sufficient opening 820 to allow passage of the cord 830 that is attached to the hand piece holder 810. The connection between the hand piece holder 810 and the housing can be a friction fit, a snap fit, or any other type of detachable connection. In some embodiments, the hand piece holder 810 can also be permanently affixed to the housing, such as with an adhesive.

One benefit of the embodiment illustrated in FIG. 6 is that it provides the dental practitioner with alternative choices for mounting the recharging docking station to accommodate different needs and preferences.

It will be appreciated that the present invention may also be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. In a dental tray system that includes a plurality of essentially identical hand piece holders each attached to a dental tray for conveniently presenting any of a plurality of different hand pieces for use in performing dental procedures, and wherein at least some of the hand pieces require electrical power, an improved tray system comprising:

a rechargeable dental curing light apparatus mountable at one end thereof in one of the essentially identical hand piece holders of the dental tray system so that the dental curing light apparatus is held in an essentially upright position similar to said some of the hand pieces requiring electrical power, said rechargeable dental curing light apparatus comprising a slender body portion that extends between a mountable end portion and a light-emitting end portion, the body portion is essentially uniform in circumference from the mountable end portion to the light-emitting end portion, the slender body portion being configured to be held in the hand of a user free from external electrical wires, and the mountable end portion of the dental curing light apparatus comprising a means for providing electrical contact for recharging the dental curing light apparatus;

a light source configured to emit radiant energy suitable for curing a light-curable compound, the radiant energy being emitted from the light-emitting end portion;

an electrically rechargeable power supply disposed within the body portion so that when used for curing a light-curing compound the dental curing light apparatus is not connected to external electrical wires; and at least one of the essentially identical hand piece holders comprising a recharging docking station comprised of:

a mounting body structure that includes an internal cavity configured in size and shape to frictionally engage the mountable end portion of the dental curing light apparatus and to hold the dental curing light apparatus at said mountable end portion so that the dental curing light apparatus extends upwardly and is presented in an essentially upright position that can be conveniently grasped;

means, located in the internal cavity of said mounting body structure, for electrically contacting the electrical contact means of the mountable end portion of the dental curing light apparatus to permit recharging the rechargeable power supply when the mountable end portion of the dental light curing apparatus is received within the internal cavity of the mounting body structure; and means for electrically connecting the means for electrically contacting the electrical contact means of the dental curing light apparatus to a source of electrical power.

2. The dental tray system that includes a rechargeable dental curing light apparatus as recited in claim 1, wherein the means for electrically contacting the electrical contact means of the mountable end portion of the dental curing light apparatus to permit recharging comprises electrical contacts disposed on or within the mounting body structure, the electrical contacts being configured to electrically couple with electrical pins extending from the mountable end portion of the light curing apparatus when the mountable end portion of the light curing apparatus is mounted within the mounting body structure of the recharging docking station.

3. The dental tray system that includes a rechargeable dental curing light apparatus as recited in claim 1, wherein the means for electrically contacting the electrical contact means of the mountable end portion of the dental curing light apparatus to permit recharging comprises electrical contacts disposed on or within the mounting body structure, the electrical contacts being configured to electrically couple with corresponding electrical contacts that circumferentially extend around the mountable end portion of the light curing apparatus when the light curing apparatus is mounted within the mounting body structure of the recharging docking station.

4. The dental tray system that includes a rechargeable dental curing light apparatus as recited in claim 1, wherein the light source comprises an LED light source.

* * * * *